US008017591B2

(12) United States Patent
Brzezicha et al.

(10) Patent No.: US 8,017,591 B2
(45) Date of Patent: Sep. 13, 2011

(54) SUBSTITUTED, NON-CODING NUCLEIC ACID MOLECULE FOR THERAPEUTIC AND PROPHYLACTIC STIMULATION OF THE IMMUNE SYSTEM IN HUMANS AND HIGHER ANIMALS (75) Inventors: Bernadette Brzezicha, Berlin (DE); Christiane Juhls, Berlin (DE); Florian Sack, Berlin (DE); Manuel Schmidt, Berlin (DE); Burghardt Wittig, Berlin (DE); Matthias Schroff, Berlin (DE)

(73) Assignee: Mològen AG, Berlin (DE)

(*) Notice: Subject to any disclaimer, the term of this patent is extended or adjusted under 35 U.S.C. 154(b) by 1369 days.

(21) Appl. No.: 11/506,766

(22) Filed: Aug. 18, 2006

(65) Prior Publication Data
US 2007/0049546 A1 Mar. 1, 2007

Related U.S. Application Data (63) Continuation-in-part of application No. PCT/DE2004/001096, filed on May 19, 2004.

(30) Foreign Application Priority Data
Feb. 20, 2004 (WO) ............... PCT/DE2004/000361

(51) Int. Cl.
A61K 48/00 (2006.01)
A61K 39/00 (2006.01)
A61K 38/00 (2006.01)
C07H 21/04 (2006.01)
(52) U.S. Cl. ................... 514/44 R; 536/24.1
(58) Field of Classification Search ................ None
See application file for complete search history.

(56) References Cited

U.S. PATENT DOCUMENTS

| 2,382,696 | A | | 8/1945 | Milleville |
| 2,699,718 | A | | 1/1955 | Wright |
| 4,363,649 | A | | 12/1982 | Yamato et al. |
| 6,589,940 | B1 | * | 7/2003 | Raz et al. ............ 514/44 R |
| 6,849,725 | B2 | * | 2/2005 | Junghans et al. ........ 536/23.1 |
| 6,849,726 | B2 | * | 2/2005 | Usman et al. ........ 536/23.1 |
| 6,977,245 | B2 | * | 12/2005 | Klinman et al. ........ 514/44 R |
| 7,378,509 | B2 | * | 5/2008 | McEvoy et al. ........ 536/23.1 |
| 7,501,503 | B2 | * | 3/2009 | Damha et al. ........ 536/24.5 |
| 7,674,777 | B2 | * | 3/2010 | Krieg et al. .......... 514/44 R |
| 2003/0125279 | A1 | * | 7/2003 | Junghans et al. ........ 514/44 |
| 2006/0183703 | A1 | * | 8/2006 | Schroff et al. ......... 514/44 |
| 2006/0241076 | A1 | * | 10/2006 | Uhlmann et al. ........ 514/44 |
| 2007/0049546 | A1 | * | 3/2007 | Brzezicha et al. ....... 514/44 |
| 2007/0142315 | A1 | * | 6/2007 | Forsbach et al. ........ 514/44 |
| 2008/0131466 | A1 | * | 6/2008 | Reed et al. ........... 424/282.1 |
| 2008/0311630 | A1 | * | 12/2008 | Schroff et al. ......... 435/91.53 |
| 2009/0004703 | A1 | * | 1/2009 | Schroff ............... 435/91.4 |
| 2009/0053250 | A1 | * | 2/2009 | Wittig et al. .......... 424/184.1 |
| 2009/0082295 | A1 | * | 3/2009 | Jungnelius et al. ....... 514/44 |
| 2009/0136528 | A1 | * | 5/2009 | Singh et al. ........... 424/185.1 |
| 2009/0181078 | A1 | * | 7/2009 | Reed et al. ........... 424/450 |

FOREIGN PATENT DOCUMENTS

| EP | 0941318 B1 | 9/1999 |
| EP | 1196178 B1 | 4/2002 |
| FR | 1418965 | 11/1965 |
| GB | 191115253 | 6/1912 |
| GB | 684057 | 12/1952 |
| WO | WO02/060476 A2 | 8/2002 |
| WO | WO03/031469 A2 | 4/2003 |
| WO | WO03/031470 A2 | 4/2003 |
| WO | WO 2006/015872 * | 2/2006 |

OTHER PUBLICATIONS

Koechling et al, Blood, Nov. 16, 2003, 102/11:746a abstract only.*
"A Heterologous Prime-Boost Regime Using DNA and Recombinant Vaccinia Virus Expressing the Leishmania Infantum P36/Lack Antigen Protects Balb/C Mice From Cutaneous Leishmaniasis," Gonzalo et al., Vaccine 20 (2002) 1226-1231.
"The Serum Mannose-Binding Protein and the Macrophage Mannose Receptor Are Pattern Recognition Molecules That Link Innate and Adaptive Immunity," Fraser et al., Immunology, vol. 10, 1998: pp. 363-372.
"Priming of Immune Responses to Hepatitis B Surface Antigen With Minimal DNA Expression Constructs Modified With a Nuclear Localization Signal Peptide," Schirmbeck et al., J. Mol. Med. (2001) 79:343-350.
"CPG Motifs: The Active Ingredient in Bacterial Extracts?", Arthur M. Krieg, Nature Medicine, vol. 9, No. 7, Jul. 2003.
"Therapeutic Vaccination Against Metastic Carcinoma by Expression-Modulated and Immunomodified Autologous Tumor Cells: A First Clinical PhaseI/II Trial," Wittig et al., Human Gene Therapy 12:267-278 (Feb. 10, 2001).
"Immune-Modulatory Function of CPG Sequence Motifs in Covalently-Closed, Double-Stem-Loop DNA Constructs (dSLIM)," Schmidt et al., Blood, vol. 102, Issue 11, Nov. 16, 2003.
European Patent Office Search Report for EP1647518A1 and English translation thereof.

* cited by examiner

Primary Examiner — Nita M Minnifield
(74) Attorney, Agent, or Firm — Ursula B. Day; Henry M. Feiereisen (57) ABSTRACT Short deoxyribonucleic acid molecules that are partially single-stranded, dumbbell shaped, and covalently closed, which contain one or more unmethylated cytosine guanosine motif (CpG motif) and exhibit immunomodifying effects. Such molecules can be used for immunostimulation applications in humans and vertebrates.

11 Claims, 4 Drawing Sheets

SEQUENCE LISTING

```
<160> NUMBER OF SEQ ID NOS: 7

<210> SEQ ID NO 1
<211> LENGTH: 58
<212> TYPE: DNA
<213> ORGANISM: Artificial
<220> FEATURE:
<223> OTHER INFORMATION: synthetic Oligodesoxynucleotide; T = chemically
      modified Thymine
<220> FEATURE:
<221> NAME/KEY: misc_feature
<222> LOCATION: (9)..(9)
<223> OTHER INFORMATION: synthetic Oligodesoxynucleotide; T = chemically
      modified Thymine

<400> SEQUENCE: 1
tcccgtggtt accaccttca ttggaaaacg ttcttcgggg cgttcttagg tggtaacc        58

<210> SEQ ID NO 2
<211> LENGTH: 58
<212> TYPE: DNA
<213> ORGANISM: Artificial
<220> FEATURE:
<223> OTHER INFORMATION: synthetic Oligodesoxynucleotide; T = chemically
      modified Thymine
<220> FEATURE:
<221> NAME/KEY: misc_feature
<222> LOCATION: (9)..(9)
<223> OTHER INFORMATION: synthetic Oligodesoxynucleotide; T = chemically
      modified Thymine

<400> SEQUENCE: 2
acgggaggtt accaccttca ttggaaaacg ttcttcgggg cgttcttagg tggtaacc        58

<210> SEQ ID NO 3
<211> LENGTH: 58
<212> TYPE: DNA
<213> ORGANISM: Artificial
<220> FEATURE:
<223> OTHER INFORMATION: unmodified synthetic Oligodesoxynucleotide
<220> FEATURE:
<221> NAME/KEY: misc_feature
<223> OTHER INFORMATION: unmodified synthetic Oligodesoxynucleotide

<400> SEQUENCE: 3
cctaggggtt accaccttca ttggaaaacg ttcttcgggg cgttcttagg tggtaacc        58

<210> SEQ ID NO 4
<211> LENGTH: 56
<212> TYPE: DNA
<213> ORGANISM: Artificial
<220> FEATURE:
<223> OTHER INFORMATION: synthetic Oligodesoxynucleotide
<220> FEATURE:
<221> NAME/KEY: misc_feature
<223> OTHER INFORMATION: synthetic Oligodesoxynucleotide
```

```
<400> SEQUENCE: 4
tccctgttac caccttcatt ggaaaacgtt cttcggggcg ttcttaggtg gtaaca        56

<210> SEQ ID NO 5
<211> LENGTH: 20
<212> TYPE: DNA
<213> ORGANISM: Artificial
<220> FEATURE:
<223> OTHER INFORMATION: synthetic Oligodesoxynucleotide; T = chemically
      modified Thymine
<220> FEATURE:
<221> NAME/KEY: misc_feature
<222> LOCATION: (12)..(12)
<223> OTHER INFORMATION: synthetic Oligodesoxynucleotide; T = chemically
      modified Thymine

<400> SEQUENCE: 5
gggagtccag ttttctggac                                                20

<210> SEQ ID NO 6
<211> LENGTH: 12
<212> TYPE: PRT
<213> ORGANISM: Simian virus 40
<220> FEATURE:
<221> NAME/KEY: MISC_FEATURE
<223> OTHER INFORMATION: NLS Peptide

<400> SEQUENCE: 6

Pro Lys Lys Lys Arg Lys Val Glu Asp Pro Tyr Cys
1               5                   10

<210> SEQ ID NO 7
<211> LENGTH: 20
<212> TYPE: DNA
<213> ORGANISM: Artificial
<220> FEATURE:
<223> OTHER INFORMATION: synthetic Oligodesoxynucleotide
<220> FEATURE:
<221> NAME/KEY: misc_feature
<223> OTHER INFORMATION: synthetic Oligodesoxynucleotide

<400> SEQUENCE: 7
aggggtccag ttttctggac                                                20
```

SUBSTITUTED, NON-CODING NUCLEIC ACID MOLECULE FOR THERAPEUTIC AND PROPHYLACTIC STIMULATION OF THE IMMUNE SYSTEM IN HUMANS AND HIGHER ANIMALS

CONTINUING APPLICATION DATA

This application is a Continuation-In-Part application of International Patent Application No. PCT/DE2004/001096, filed on May 19, 2004, which claims priority from International Patent Application No. PCT/DE2004/000361, filed on Feb. 20, 2004. International Patent Application No. PCT/DE2004/001096 was pending as of the filing date of this application. The United States was an elected state in International Patent Application No. PCT/DE2004/001096.

BACKGROUND

1. Technical Field

This application concerns a substituted, non-coding nucleic acid molecule for modulation of the activity of the human or animal immune system, as well as a method to make such molecule and a vaccine containing the substituted, non-coding nucleic acid molecule.

2. Background Information

In the formation of an immune response against an antigen, two major branches of the immune system are distinguished: on one side, the humoral arm, which relies on the synthesis of antibodies by B lymphocytes, but also a humoral component of non-adaptive immunity, the complement system. On the other side, the cellular arm relies on the activity of T lymphocytes, NK cells and antigen presenting cells of the immune system. T lymphocytes are capable of recognizing cells that are infected by virus. Correspondingly, the cellular arm is also referred to as the $T_H1$ response and the humoral arm as the $T_H2$ response.

Bacteria and parasites that predominantly exist extracellularly are usually fought by the $T_H2$ arm. Pathogens that predominantly reside intracellularly, as is the case for some bacterial species and all viruses, however, are mainly fought by the $T_H1$ arm, mainly meaning by cytotoxic cells.

The development of vaccines has continuously delivered vaccines that are more efficacious and at the same time show lesser side effects. Departing from attenuated live vaccines or inactivated pathogens, vaccines were developed that consist of antigens made by recombinant methods (for example against Hepatitis B virus, recombinant vaccines against herpes simplex virus, human papilloma virus (cervical carcinoma) and borrelia are in clinical development). These vaccines lead to a predominantly $T_H2$ dominated immune response and need the co-application of adjuvants in order to attain stable immunity. These adjuvants thus lead to a balance of humoral and cellular immune response.

Some infectious diseases can only be prevented by vaccination, if the vaccine elicits a $T_H1$ dominated immune response. For such vaccines, the combination of a DNA vaccine (induction of cellular immunity) with a recombinant antigen (induction of humoral immunity) is currently regarded as the optimal combination (Esteban et al., Vaccine 2002, 20: 1226-1231). The recombinant protein, which is difficult and costly to synthesize, is the decisive cost factor in this process. Peptides, which are less expensive to make, are only of limited utility since they induce a shift towards a $T_H2$ dominated immune response.

Despite all progress in DNA vaccination, a real breakthrough has not been achieved until today. Several reasons exist for this fact, among them insufficient transfection and a resulting low level of expression of the vaccinated antigen, as well as a globally insufficiently pronounced immune response as a result of the vaccination.

In order to improve the transfection efficiency, different peptides and other organic molecules have been linked to gene transfer vehicles by different methods of coupling. Also, it was tried to utilize ligand-receptor interactions for improved uptake of gene transfer vehicles by coupling of ligands (Fraser et al., 1998, Semin. Immunl., 10 (5): 363-72).

By attaching the nuclear localization signal (NLS) of the SV-40 virus covalently to expression cassettes encoding the small surface antigen of Hepatitis (HBsAg), a 10 to 15-fold increased antibody titre could be demonstrated after intramuscular application (Schirmbeck et al., J. Mol Med. June 2001; 79 (5-6):343-50).

In order to avoid the disadvantages of current viral and plasmid-based gene transfer systems, covalently closed, minimalistic DNA expression constructs were developed (see EP 0 914 318 B1). These minimalistic expression constructs can also be linked covalently to a nuclear localization signal of the SV-40 virus and then lead to a shift towards a $T_H1$ accentuated immune response (see WO 03/0031469).

In order to generate an improved immune response, CpG oligonucleotides (CpG-ODN) were employed as a new class of immune modulating molecules. Such unmethylated CpG motifs occur in bacterial DNA and constitute a danger signal for the immune system. As a pathogen associated molecular pattern (PAMP), they mainly result in an unspecific activation of the innate immune system (Krieg, Nat. Med 2003, 9: 831-835).

CpG ODN also induce a $T_H1$-biased immune response by means of the cytokines interleukin-12, interferon gamma and tumor necrosis factor alpha.

Immune stimulatory nucleic acid sequences (ISS) that comprise the described CpG ODN are only a few bases in length and do not function through the expression of proteins encoded thereon.

The ISS used herein are dumbbell-shaped, covalently closed deoxyribonucleic acid molecules. They consist of oligonucleotides, the bases of which can partially form pairs with each other, and one or two hairpin loops that comprise 30 bases and contain several CpG motifs (see EP 1 196 178). It was demonstrated that the immune modulating effect of these dumbbell-shaped covalently closed deoxyribonucleic acid molecules is strongly dependent on the loop-double strand combination and the CpG motifs contained therein. Linearization, deletion of a hairpin loop, downsizing of the molecule or the removal of CpG motifs lead to a changed pattern of induction of cytokines.

The strong stimulation of the cellular immune response facilitates an influence on regulatory cycles that would, in the absence of interference, not lead to an immune activity that would be satisfactory to the patient.

These dumbbell-shaped, covalently closed and non-coding nucleic acid molecules, which comprise at least one or more CpG motifs and single stranded hairpin loops on one or both ends, are referred to synonymously as "carrier molecules" in the following.

In this context, the term "nucleic acids" is to be understood as meaning deoxyribonucleic acids.

Immune stimulation in the context of this invention means that the mediator and effector cells of the immune system, i.e. in particular the currently known thymocytes that possess a helper function, and cytotoxic thymocytes, B cells and so-called NK (natural killer) cells, macrophages and monocytes, as well as dendritic cells and their precursors, as well as functionally as yet unexplained cell populations with functions within the immune system, as described in the invention, are stimulated by nucleic acid molecules in order to proliferate, migrate, differentiate or become active. Immune modulation means that, besides providing general stimulation in the above-defined sense, the nature or character of an immune reaction is influenced, either by affecting an immune reaction that is currently still developing or maturing, or by modulating the character of a reaction that has already established itself.

Short nucleic acid molecules in the context of the present invention are such molecules having a chain length as given in the examples below (preferably 48 to 116 nucleotides).

OBJECT OR OBJECTS

Departing from this state of the art, it is the objective of the present invention to provide suitably modified carrier molecules that are capable of inducing an efficient immune response, as well as a method to synthesize these modified carrier molecules, and vaccines containing the modified carrier molecules.

SUMMARY

This objective is obtained by providing a non-coding nucleic acid molecule, which comprises or essentially consists of a chain of partially single-stranded, dumbbell-shaped deoxyribonucleotide residues and contains one or more sequences of the base sequence $N^1N^2CGN^3N^4$ in its single or double stranded region, where $N^1N^2$ is an element chosen from the group comprising GT, GG, GA, AT or AA, $N^3N^4$ is an element chosen from the group comprising CT or TT, and C is deoxycytosine, G is deoxyguanosine, A is deoxyadenosine and T is deoxythymidine and which is coupled to one or more substituents by covalent linkage.

Depending on the embodiment of the deoxyribonucleic acid molecule, the covalently linked substituent is selected from the group comprising peptides (including cationic peptides), proteins, saccharides, antigenic structures, DNA and/or RNA.

In one embodiment of the inventive nucleic acid molecule, in which more than one substituent is attached covalently, these substituents can be chosen from the same or from different groups. In the case of such a deoxyribonucleic acid molecule being linked to several substituents covalently, these can be identical or different from each other.

In another embodiment of the nucleic acid molecule both the substituent or the substituents and the nucleotides, to which the substituents are chemically linked, are chemically modified. It is also conceivable, however, that only one of the two partners needs to be modified chemically in order to attain the desired covalent coupling. Furthermore, it is also possible that the linkage between substituent and nucleotide is achieved by employing a bi-functional coupling reagent.

The nucleic acid molecules can be synthesized by a method comprising the following procedural steps:
 a. two oligodeoxyribonucleotides, which are partially self-complimentary and of which at least one is chemically modified, are brought to react under suitable reaction conditions with chemically modified substituents selected from the group comprising peptides (including cationic peptides), proteins, saccharides, antigenic structures, DNA and/or RNA, where said chemically modified oligodeoxyribonucleotide or -nucleotides become covalently attached to the substituent directly or by means of a bi-functional coupling reagent,
 b. subsequently, the purified products of the coupling reaction are allowed to form base pairs partially and to form hairpin structures by brief heating and subsequent chilling on ice and
 c. the resulting self-complementary overhangs of the partially double-stranded non-coding nucleic acid molecules are ligated to each other or to oligodeoxynucleotides that are coupled to other substituents,
 d. followed by a treatment with exonuclease in order to digest chains of not covalently closed oligodeoxyribonucleotides that are coupled to a substitute, before
 e. finally the non-coding nucleic acid molecules that are linked to substituent are purified.

The method employs oligodeoxynucleotides for the coupling of a substituent that are chemically modified by one or more alcylic carbonic acid, amine, thiol or aldehyde functionalities, or a maleimide group. Depending on the embodiment of the nucleic acid molecule that is to be synthesized, also substituents can be employed that are chemically modified by one or more alcylic carbonic acid, amine, thiol or aldehyde functionalities, or a maleimide group.

Nucleic acid molecules in accordance with at least one possible embodiment can be employed as an adjuvant in the therapeutic or prophylactic vaccination of humans or higher animals. Furthermore, the use of the inventive nucleic acid molecules is conceivable for immune stimulation in humans and higher animals, in which case this stimulation can be effected in-vitro or in-vivo.

Nucleic acid molecules in accordance with at least one possible embodiment can also be a component of a vaccine that is employed in order to modulate the immune response in humans or higher animals.

It is also provided that this vaccine comprises a combination of nucleic acid molecules as in accordance with at least one possible embodiment and dumbbell shaped, linear covalently closed DNA expression constructs, which are linked to substituents. This combination vaccine can be employed as a vaccine in the therapeutic or prophylactic vaccination of humans or higher animals or as an adjuvant for the stimulation of the immune response in humans or higher animals, both in-vivo and in-vitro.

In accordance with at least one possible embodiment, at least one objective is attained by synthesizing short, non-coding nucleic acid molecules, which comprise at least one or several CpG sequences, said molecules also being termed "carrier molecules," and which are attached to at least one or several substituents selected from the class of peptides (including cationic peptides), proteins, saccharides, antigenic structures, DNA and/or RNA by covalent coupling. Furthermore, the provision of a new vaccine combination comprising carrier molecules with attached substituents in accordance with at least one possible embodiment, and minimalistic DNA expression vectors that are modified by substituents, is envisioned.

Said short, non-coding nucleic acid molecules comprise a partially single-stranded, dumbbell-shaped sequence of nucleoside residues and contain one or more sequences of the base sequence $N^1N^2CGN^3N^4$, where $N^1N^2$ is an element of the GT, GG, GA, AT or AA group, $N^3N^4$ is an element of the CT or TT group, as well as C deoxycytosine, G deoxyguanosine, A deoxyadenosine and T deoxythymidine. It is possible to obtain covalently closed deoxyribonucleic acid molecules of this kind from open-chained deoxyribonucleic acid molecules, which exhibit a partially self-complementary sequence and which, either together with each other or with a second molecule, are able to create with an intermediary stable hybrid which has a closed double-stranded area with a gap in the sugar phosphate backbone, by ligation of the gap in the backbone using a suitable enzyme, for instance a DNA ligase derived from a T4 bacteriophage. Alternatively, a molecule in accordance with at least one possible embodiment can also be obtained by intra-molecular ligation of a molecule which has at least two self-complementary areas, separated only by a gap in the phosphate backbone.

Thus, the covalent attachment of substituents to this carrier molecule and the new qualities of the corresponding molecule resulting therefrom are essential. The attachment can be effected to any nucleotides of the stem or the loops (the hairpin shaped single stranded regions). In the example given below, covalent attachment is effected by means of an inserted sulfhydryl group (SH group) on the thymine; the attachment by means of a bi-functional coupling reagent is also conceivable. Other alternatives are possible and not excluded by the description. The examples given below are thus not exclusive.

Any substituent selected from the group of peptides (including cationic peptides), proteins, saccharides, antigenic structures, DNA and/or RNA that was modified with an maleimide group on the amino terminus can be used for attachment.

The NLS (nuclear localization sequence from the SV-40 virus) peptide shall be exemplary for understanding the term substituent. A covalent attachment of the carrier molecule to the NLS peptide leads to a synergistic effect in the induction of an immune response through the structural elements that were described (combination of double strand, hairpin loop and CpG ODN). The adjuvant effect of the carrier molecules is significantly enhanced by the attachment of the NLS peptide. In-vitro stimulation assays with B cells demonstrated a more than 50% increase of the expression of the surface marker CD80 when the inventive molecules were used, in comparison to controls (see FIG. 2).

Furthermore, antigens or epitopes thereof that are useful for the provocation of a protective immune response shall be understood as falling under the definition of substituent. As an example and not exclusively, antigenic epitopes of human papilloma virus, influenza virus, for example immunogenic epitopes of the proteins H, M1 and NP, of the SARS virus, for example immunogenic epitopes of the proteins S, M, and N, of m. tuberculosis, the HI virus, hepatitis B virus, furthermore antigenic epitopes of parasitic diseases such as leishmaniasis as well as the group of tumor associated antigens (TAA) as they are known from tumor diseases.

The advantages of the attachment of carrier molecules to one or several antigenic epitopes, either in the double stranded region or in the hairpin loop, are on one hand the induction of an antigen-specific immune response of the adaptive immunity, and on the other hand the activation of the innate immune system. Additionally, a $T_H1$ dominated immune response is enhanced by a corresponding secretion of cytokines. This combined induction of a fast, unspecific immune modulation triggered by the carrier molecule, with a delayed specific immune response triggered by the substituent, in this case certain antigenic epitopes, allows to employ these molecules also in the event of acutely impending infection.

The attachment of different, not identical substituents to the carrier molecule is explicitly provided. Examples of these nucleic acid carrier molecules that are attached to substituents are given in FIG. 3, without limiting the scope of the application to these examples.

A further aspect of at least one possible embodiment is the combined use of the nucleic acid carrier molecules that are attached to substituents with minimalistic, linear DNA expression vectors that are attached to substituents, which carry the genetic information for a corresponding antigen. This combination vaccine is outlined in FIG. 4. One or several identical or different substituents can be attached covalently to these DNA expression vectors. The substituents are selected from the group of peptides (including cationic peptides), proteins, saccharides, antigenic structures, DNA and/or RNA. The expressed antigen and the antigen that is attached as a substituent can be the same antigen. It is also provided that expressed antigen and the substituent attached to the DNA expression construct are not identical and selected from different groups.

Such a vaccine can activate the innate immune system by the component of the carrier molecule that is attached to substituents and is thus capable to confer protection against viral, parasitic and bacterial infections in 24-48 h. The second component, the DNA expression constructs that are attached to substituents, mediate antigen-specific immunity. Thus, specific antibody production and formation of a cytotoxic immune response within two weeks of vaccination is attained.

This combination of vaccines leads to a variable vaccine consisting of antigen expressing minimalistic expression constructs and carrier molecules that are attached to substituents, with a rapid onset of effect. The substituent attached to the carrier molecule and to the DNA expression construct can be the same substituent that is expressed by the DNA expression vector as an antigen, but the expressed antigens can be different from the substituents.

One or several identical or different substituents can be attached covalently to the carrier molecules. In the case of identical substituents being attached to a carrier molecule, it is provided that these are mixed with other carrier molecules that bear different substituents and that the resulting mix comprising different substituents is then applied.

A schematic depiction of the molecules in accordance with at least one possible embodiment is shown in FIG. 4.

Advantageously, the molecules in accordance with at least one possible embodiment have no free 5'- or 3'-ends and thus are inaccessible to exonucleases.

The nucleic acid molecules can comprise the following sequences, depending on the embodiment,

```
(Seq ID. 1)
5'Ph-TCC CGT GGT TAC CAC CTT CAT TGG AAA ACG TTC

TTC GGGGCG TTC TTA GGT GGT AAC C
or
(Seq ID. 2)
5'Ph-ACG GGA CC TTAC CAC CTT CAT TGG AAA ACG TTC

TTC GGGGCG TTC TTA GGT GGT AAC C.
```

The claimed nucleic acid molecules having the specific sequences or sequence regions given above preferably comprise a length of up to 200, especially preferred of 48 to 116 nucleotides.

Further advantageous measures are described herein below; at least one possible embodiment is described in more detail in the following figures and in examples.

The above-discussed embodiments of the present invention will be described further hereinbelow. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

FIG. 3 shows schematically the possibilities to attach identical and different substitutes to carrier molecules. In particular, it is shown as
  A: a carrier molecule with two hairpin loops, CpG motifs contained therein depicted as grey circles, and having two different substituents that are attached to the double stranded region of the carrier molecule.
  B: a carrier molecule with two hairpin loops, CpG motifs contained therein depicted as grey circles, and having two different substituents that are attached to the single stranded hairpin loop region of the carrier molecule.
  C: a carrier molecule with two hairpin loops, CpG motifs contained therein depicted as grey circles, and having two similar substituents that are attached to the double stranded region of the carrier molecule.
  D: a carrier molecule with two hairpin loops, CpG motifs contained therein depicted as gray circles, and having two similar substituents that are attached to the single stranded hairpin loop region of the carrier molecule.

DESCRIPTION OF EMBODIMENT OR EMBODIMENTS

Example 1

Figure 1:
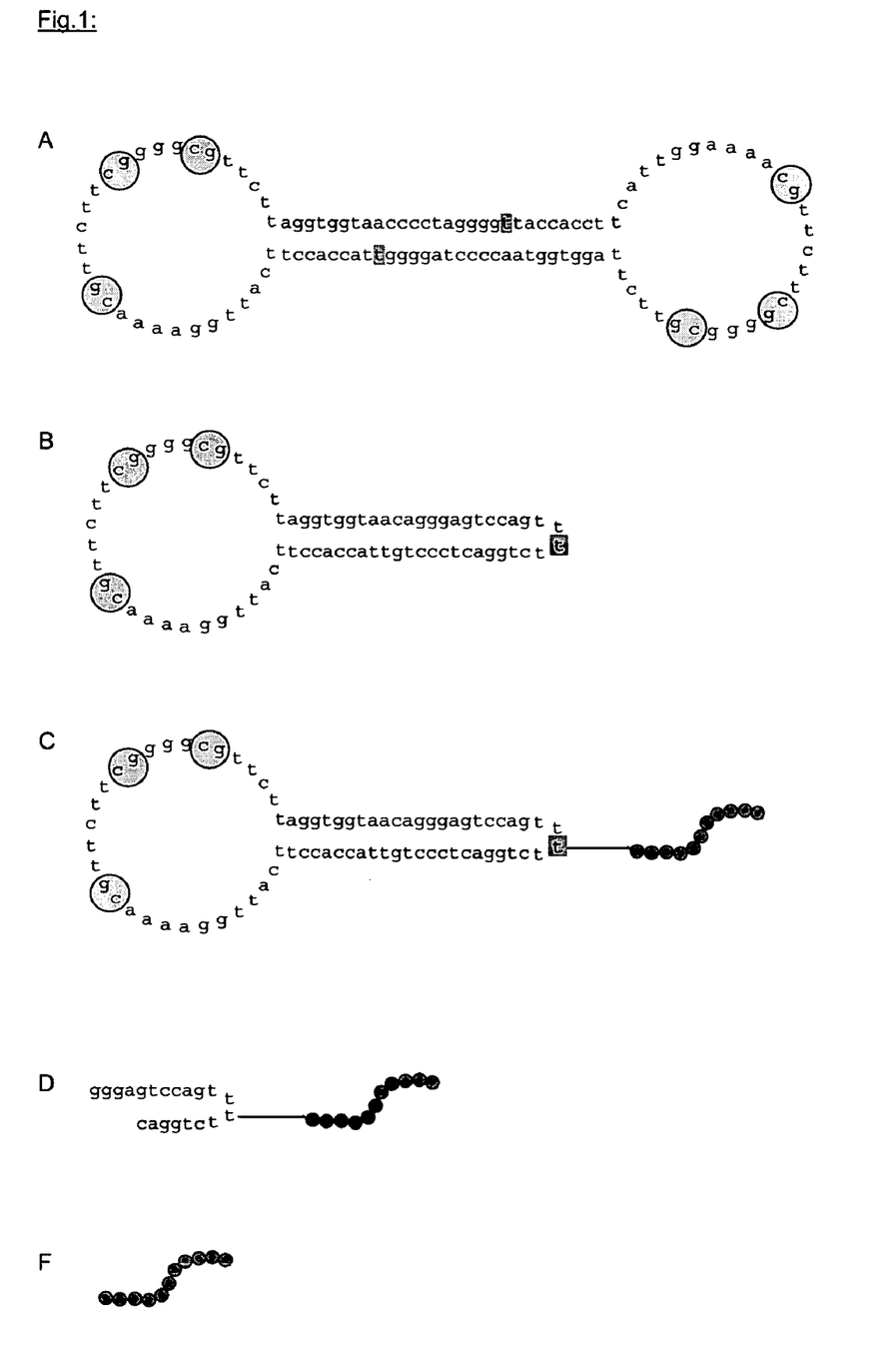
FIG. 1 shows, in an exemplary fashion, possible carrier molecules and a carrier molecule that is attached to substituents. One structural feature of the carrier molecules, the CpG motifs, is emphasized by circles in the hairpin loops. The nucleotide thymine that was used in the examples to attach the respective substituent is shaded in grey, whereas any other nucleotide is similarly useful. The attachment of a substituent can be achieved in several places within the hairpin loops, the attachment can also be achieved in the double stranded region of the carrier molecules. In particular, it is shown as
  A: carrier molecule with demarcated possible positions of attachment in the double stranded region and three CpG motifs in each hairpin loop.
  B: carrier molecule with one hairpin loop
  C: carrier molecule that is attached to substituents with one hairpin loop
  D: shows one substituent attached to ODN that served as control in example 6
  F: shows one substituent that served as control in example 6.
Figure 2:
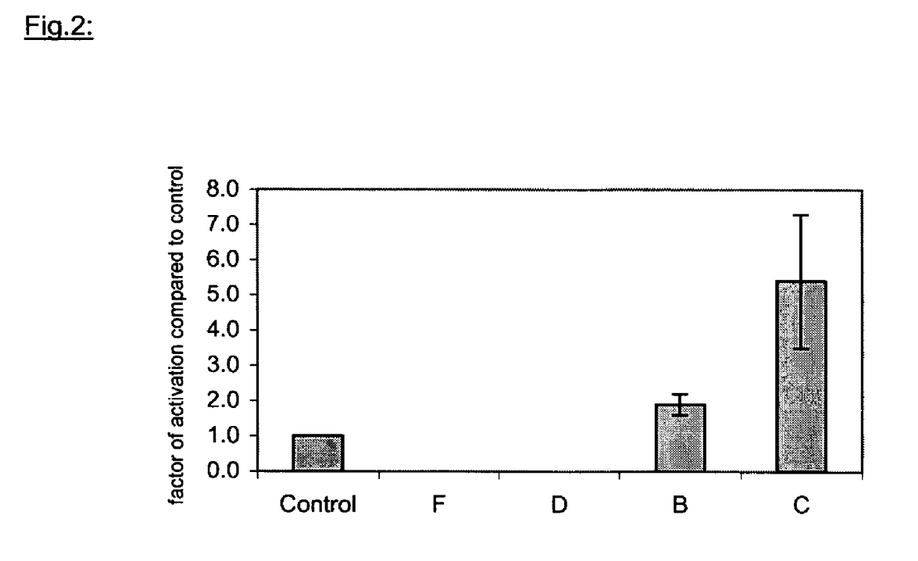
FIG. 2 determination of the immune stimulating effects of the carrier molecules that are attached to substituents was performed in the framework of stimulation assay with B cells. The following samples were used:
  Control: B cells without addition of sample
  F: NLS peptide
  D: ODN attached to NLS peptide
  B: carrier molecule with one hairpin loop
  C: carrier molecule with NLS attached
  On the x co-ordinate, the ratio of sample value and control value is shown. The bars show the results of the in-vitro experiment by reading out the stimulated expression of the surface marker CD80. Samples F and D are also used as a control and show no stimulation. The NLS peptide alone and the NLS peptide attached to an ODN are not capable to stimulate B cells to increased secretion of CD80. The carrier molecule with a hairpin loop and without NLS peptide leads to an increased secretion of CD80. With the inventive NLS-attached carrier molecule, this stimulating effect is increased by the factor 3. The experiment shows that only the combination of the components double strand, single-stranded hairpin loop, CpG motifs and the covalent attachment of substituents, in this case NLS peptide, lead to a surprising result.
Figure 3:
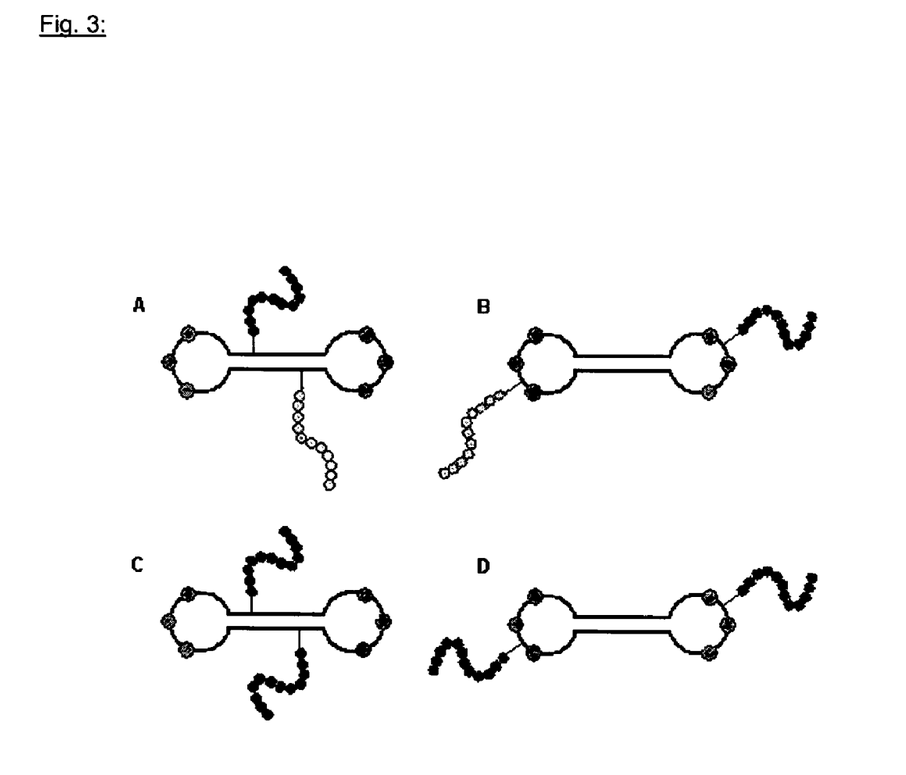
Figure 4:
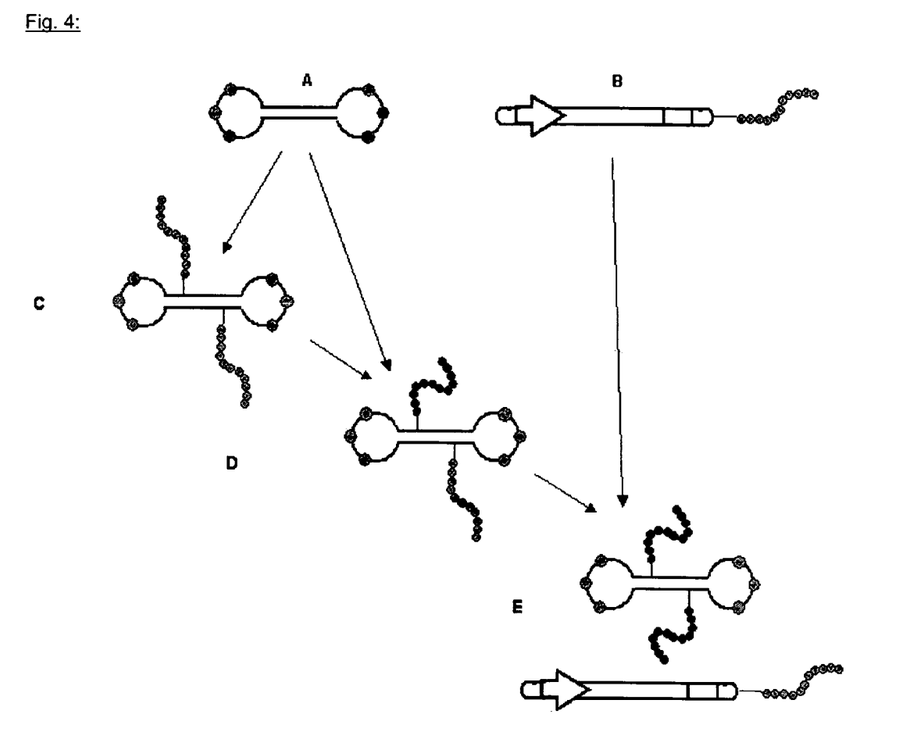
FIG. 4 shows the carrier molecules that are attached to substituents in accordance with at least one possible embodiment and the combination vaccine in overview. In particular, it is shown as
  A: a carrier molecule consisting of a combination of single stranded hairpin loop and double strand, containing CpG motifs (schematically depicted as circles).
  B: a minimalistic, covalently closed DNA expression construct that is attached to a substituent.
  C: a carrier molecule attached to substituents that is attached to two similar substituents in the double stranded region.
  D: a carrier molecule attached to substituents that is attached to different substituents in the double stranded region.
  E: shows the combination of a carrier molecule attached to substituents and a DNA expression construct attached to substituents. The substituents of the two molecules are different, but can also be the same.

Synthesis of Unmodified Carrier Molecules According to EP1196178

Phosphorylated ODN (SeqID.3) of the sequence CCTAGGGGTT ACCACCTTCA TTGGAAAACG TTCTTCGGGG CGTTCTTAGG TGGTAACC (TIB-Molbiol, Berlin) are heated to 90° C. for 5 min and subsequently chilled on ice to facilitate the formation of a hairpin structure. Self-complementary overhangs were ligated with a final concentration of 1 µg/µl DNA in the presence of T4 DNA ligase (0.1 U/µg ODN) at 37° C. for 24 hours. The product was obtained following phenol extraction and subsequent extraction with chloroform as well as isopropanol precipitation in the presence of $MgCl_2$ (f.c. 10 mM) and NaAc (f.c. 300 mM), and after centrifugation and suspension in water.

In order to remove endotoxin contamination, the ligation product was subjected to subsequent anion exchange chromatography (carrier substance: LiChrospher DMAE, Merck Darmstadt; 0-1M NaCl in 50 mM NaPhosphate) and concentrated by isopropanol precipitation. For in vivo experiments this method is carried out in sterile conditions and the end product is suspended in sterile PBS.

Example 2

Synthesis of Carrier Molecules that are Attached to Substituents by Two Different Reaction Pathways a) and b)

a) Attachment of Maleimide Functionalized Substituents to Thiole Groups (SH) of Modified Deoxyribonucleotides The sulfhydryl group of the SH-ODN was capped with the protective group dimethoxytrityl (DMT) due to its high innate reactivity. This protective group is removed prior to reaction.

For the synthesis of carrier molecules that are attached to substituents, different ODN are used in example 1 that all guarantee a defined modification of the SH-ODN. A defined attachment either is performed in the stem or the loops or in both stem and loops. For this purpose, ODN 1 and 2 are employed:

```
ODN 1 (Seq ID. 1):
5'Ph-TCC CGT GG XT TAC CAC CTT CAT TGG AAA ACG TTC
TTC GGGGCG TTC TTA GGT GGT AAC C
and
ODN 2 (Seq ID. 2):
5'Ph-ACG GGA GG XT TAC CAC CTT CAT TGG AAA ACG TTC
TTC GGGGCG TTC TTA GGT GGT AAC C
```

(provided by Eurogentec, Belgium), where XT is SH-modified T and Ph is 5'-phosphorylation.

In order to remove the protective group DMT the SH-ODN was dissolved in deprotection buffer (4 mM $K_2HPO_4$, 4 mM $KH_2PO_4$, pH 6.8) and 120 mM silver nitrate ($AgNO_3$) was added. This reaction was incubated at room temperature for 30 min. Thereafter, the deprotection reaction was mixed with 0.2 volumes DTT and incubated at room temperature for 20 min. The reaction was briefly centrifuged and the supernatant was given onto a gel filtration column (NAP-5, Amersham Biosciences) in order to purify the deprotected SH-ODN.

The deprotected SH-ODN were reacted in coupling buffer (100 mM $Na_2HPO_4$, 150 mM NaCl) with the maleimide-modified substituent. The reaction was incubated at room temperature for one hour in order to let the maleimide group react with the SH group. In principle, the use of other ODN that contain SH groups, protected or unprotected, is possible. The attachment of SH groups to a maleimide substituent is only an example for the groups of all maleimide-containing substituents.

b) Attachment of Thiole Groups Containing Substituents by Means of Bi-Functional Cross-Linking Molecules to Amino-ODN For the conceptual verification, the reaction of a thiole group present on the substituent that was to be attached, with a maleimide group on the ODN was employed. The maleimide group was introduced into the nucleic acid component of the reaction by reacting an amino residue (termed X) that had been inserted into the ODN at the time of synthesis with a commercially available bi-functional coupling reagent by transamidation of the NHS carboxylic acid present in the coupling reagent. For the synthesis, the following amino-modified ODN were employed:

```
ODN 1 (Seq ID. 1):
5'Ph-TCC CGT GGXT TAC CAC CTT CAT TGG AAA ACG TTC
TTC GGGGCG TTC TTA GGT GGT AAC C
and
ODN 2 (Seq ID. 2):
5'Ph-ACG GGA GGXT TAC CAC CTT CAT TGG AAA ACG TTC
TTC GGGGCG TTC TTA GGT GGT AAC C
```

(provided by Eurogentec, Belgium), where XT is NH-modified T and Ph is 5'-phosphorylation.

The amino modified ODN were used in the coupling as follows: the cross-linking molecule (here: sulfo-KMUS (N-(maleimidoundecanoyloxy)sulfosuccinimide) in DMSO, PIERCE Product-Nr. 21111) was added in four equal parts to the reaction at intervals of 30 min to the amino-ODN (0.1 mM final conc.), until a final concentration of 5 mM was reached. The reaction took place in a cross-linking coupling buffer (50 mM $NaHPO_4$, 75 mM NaCl, pH 7.6) at 37° C. for two hours. Subsequently, the reaction was stopped by addition of Tris-HCl (pH 7.5; 50 mM f.c.). The activated amino-ODN were precipitated in −70° C. ethanol for 30 min (300 mM NaOAc pH 5.3; 20 mM $MgCl_2$; 2.5-fold reaction volume 100% ethanol abs.). The precipitate was spun for 30 min at 15,000 rpm (4° C.) and washed under similar conditions in 70% ethanol for 15 min. The activated amino-ODN were dissolved in coupling buffer (1x=50 mM $NaHPO_4$, 75 mM NaCl, pH 7.0) to a final concentration of 0.1 mM. The thiole substituent (provided by Dr. Peter Henklein, Charité, Berlin) was added in 0.2 mM final concentration. The reaction proceeded at 37° C. for one hour.

The purification and separation of the resulting ODN with attached substituent from the unreacted ODN was performed by reversed phase HPLC. Single fractions were analyzed by gel electrophoresis. The HPLC fractions containing the ODN with attached substituents were concentrated in a vacuum centrifuge and resuspended in ultrapure water (Millipore MilliQ). ODN with attached substituents were purified on a Nukleosil-300 C18 column (10 micromole, 250 mm×8 mm bore) by HPLC. The gradient went from 0% buffer A (100 mM ammonium carbonate) to 42% buffer B (80% acetonitrile) in 47 min at a flow rate of 2.4 ml/min.

The ODN with attached substituents that had been synthesized according to examples 2a and 2b were heated to 90° C. for 5 min and subsequently chilled on ice to facilitate the formation of a hairpin structure. Self-complementary overhangs were ligated with a final concentration of 0.55 µg/µl DNA in the presence of T4 DNA ligase (0.01 U/µg ODN) at 37° C. for 24 hours. After heat inactivation (68-72° C.) of the T4 ligase for 20 min a T7 DNA Polymerase digest was performed (0.025 U/µg ODN) at 37° C. for 12 hours in order to remove ODN with attached substituents that were not covalently closed. The product was obtained following phenol extraction and subsequent extraction with chloroform as well as isopropanol precipitation in the presence of $MgCl_2$ (f.c. 10 mM) and NaAc (f.c. 300 mM), and after centrifugation and suspension in water.

In order to remove endotoxin contamination, the ligation product was subjected to subsequent anion exchange chromatography (carrier substance: Fractogel DMAE, Merck Darmstadt; 0-1M NaCl in 20 mM Tris/HCl pH7.0) and concentrated by isopropanol precipitation. For in vivo experiments this method is carried out in sterile conditions and the end product is suspended in sterile PBS.

Example 3

Synthesis of Carrier Molecules with a Loop that are Attached to Substituents

```
ODN 3 (Seq ID. 4):
5'Ph-TCC CTG TTA CCA CCT TCA TTG GAA AAC GTT CTT
CGG GGC GTT CTT AGG TGG TAA CA
and
ODN 4 (Seq ID. 5):
5'Ph-GGG AGT CCA GT XTT TCTG GAC
```

(provided by Eurogentec, Belgium), where XT is NH-modified T and Ph is 5'-phosphorylation.

The ODN 4 (SeqID.5) was attached by means of an NH group and the bi-functional cross-linker sulfo-KMUS to the peptide NLS (PKKKRKVEDPYC (SeqID.6, provided by Peter Henklein, Charité, Berlin) and the thiol of the cysteine group according to the coupling mechanism described in 2b. Ligation and the subsequent steps proceeded as described.

Example 4

Synthesis of Minimalistic, Covalently Closed DNA Expression Constructs for the Combination Vaccine The DNA expression constructs employed herein are linear, covalently closed expression cassettes consisting of the CMV promoter, an intron, the gene sequence encoding an antigen and a polyadenylation sequence (see EP 0 941 318 B1). A suitable plasmid comprising the respective sequence was digested to completion by Eco31I. Ligation with a 5'-phosphorylated
ODN 5 (SeqID.7):
5'-Ph-AGG GGT CCA GTT TTC TGG AC (provided by Eurogentec, Belgium)
was performed with T4 DNA ligase in the presence of Eco 31I and was stopped by heating to 70° C. The resulting mix was concentrated and treated with Eco 31I and T7 DNA polymerase in the absence of deoxyribonucleotide triphosphates. Purification was performed by anion exchange chromatography.

Example 5

Synthesis of Minimalistic, Covalently Closed DNA Expression Constructs with Substituent For the synthesis of minimalistic, covalently closed DNA expression constructs, in this example with NLS peptide as a substituent, ODN 4 (SeqID.5) bearing in the hairpin loop a deoxy uracil modified by an amino group (XT) and the non-modified ODN 5 (SeqID.7) were employed:

```
ODN 4 (Seq ID. 5):
5'-Ph-GGG AGT CCA GT XT TTC TGG AC
```

(provided by Eurogentec, Belgium), where XT is NH-modified T and Ph is 5'-phosphorylation.
and
ODN 5 (SeqID.7):
5'-Ph-AGG GGT CCA GTT TTC TGG AC (provided by Eurogentec, Belgium)

The amino-modified ODN 4 was employed in the coupling reaction as follows: the cross-linking molecule (here: sulfo-KMUS (N-(maleimidoundecanoyloxy)sulfosuccinimide) in DMSO, PIERCE Product-Nr. 21111) was added in four equal parts to the reaction at intervals of 30 min to the amino-ODN (0.1 mM final conc.), until a final concentration of 5 mM was reached. The reaction took place in a cross-linking coupling buffer (50 mM NaHPO$_4$, 75 mM NaCl, pH 7.6) at 37° C. for two hours. Subsequently, the reaction was stopped by addition of Tris-HCl (pH 7.5; 50 mM f.c.). The activated amino-ODN were precipitated in −70° C. ethanol for 30 min (300 mM NaOAc pH 5.3; 20 mM MgCl2; 2.5-fold reaction volume 100% ethanol abs.). The precipitate was spun for 30 min at 15,000 rpm (4° C.) and washed under similar conditions in 70% ethanol for 15 min. The activated amino-ODN were dissolved in ultra-pure water (MilliQ, Millipore) and frozen until further coupling at −20° C.

Example 5a

Attachment of NLS Peptide to Activated ODN

The activated amino ODN described under 5 were dissolved in coupling buffer (1x=50 mM NaHPO$_4$, 75 mM NaCl, pH 7.0) to a final concentration of 0.1 mM. The NLS peptide PKKKRKVEDPYC (provided by Dr. Peter Henklein, Charité, Berlin) was dissolved in water and added in 0.2 mM final concentration. The reaction proceeded at 37° C. for one hour.

The purification and separation of the resulting ODN with attached NLS from the unreacted ODN was performed by reversed phase HPLC. Single fractions were analyzed be gel electrophoresis. The HPLC fractions containing the ODN with attached substituents were concentrated in a vacuum centrifuge and resuspended in ultrapure water (Millipore MilliQ). Modified ODN were purified on a Nukleosil-300 C18 column (10 micromole, 250 mm×8 mm bore) by HPLC. The gradient went from 0% buffer A (100 mM ammonium carbonate) to 42% buffer B (80% acetonitrile) in 47 min at a flow rate of 2.4 ml/min.

The minimalistic covalently closed DNA expression constructs with NLS substituent were obtained as follows: after preparation of the expression cassette by Eco31I digest, according to example 4, ligation with the prepared ODN was performed. Ligation with 5' phosphorylated hairpin-shaped ODN 4, which was attached to the NLS peptide and ODN 5 was achieved by T4 DNA ligase in the presence of Eco 31I and subsequently stopped by heating to 70° C. The resulting mix was concentrated and treated with Eco 31I and T7 DNA polymerase in the absence of deoxyribonucleotide triphosphates. Purification was performed by anion exchange chromatography. Proof of successful attachment of the substituents to the DNA expression constructs was performed by restriction digest, which confirmed the successful attachment.

Example 6

Stimulation of Immunologically Relevant Surface Proteins by Carrier Molecules that are Attached to Substituents A control of the functionality of the carrier molecules that are attached to substituents was performed by means of a stimulation assay with B cells. The incubation of RPMI-8226 cells (a cell line of the B lineage) was performed over 48 h with equimolar amounts of the molecules (1 μmole). The analysis of the results was performed by FACS measurement. The values thus obtained refer to the unstimulated state (control). The surface marker CD80 was determined as % positive cells.

One feature or aspect of an embodiment is believed at the time of the filing of this patent application to possibly reside broadly in a non-coding nucleic acid molecule, which consists of a partially single-stranded, dumbbell-shaped covalently closed chain of deoxyribonucleotide residues and contains one or more sequences of the base sequence $N^1N^2CGN^3N^4$ in its single or double stranded region, where $N^1N^2$ is an element chosen from the group comprising GT, GG, GA, AT or AA, $N^3N^4$ is an element chosen from the group comprising CT or TT, and C is deoxycytosine, G is deoxyguanosine, A is deoxyadenosine and T is deoxythymidine, characterized by one or more substituents being attached covalently to said non-coding nucleic acid molecule.

Another feature or aspect of an embodiment is believed at the time of the filing of this patent application to possibly reside broadly in the deoxyribonucleic nucleic acid molecule, where the substituent is selected from the group of peptides, proteins, saccharides, antigenic structures, DNA and/or RNA.

Yet another feature or aspect of an embodiment is believed at the time of the filing of this patent application to possibly reside broadly in the deoxyribonucleic nucleic acid molecule, where in the case of covalent attachment of more than one substituent, these are selected from the same or different groups.

Still another feature or aspect of an embodiment is believed at the time of the filing of this patent application to possibly reside broadly in the deoxyribonucleic nucleic acid molecule, where several substituents originating from one of the groups named in claim 2 are identical or different from each other.

A further feature or aspect of an embodiment is believed at the time of the filing of this patent application to possibly reside broadly in the deoxyribonucleic nucleic acid molecule, where chemically modified substituents and/or chemically modified nucleotides are covalently attached to each other.

Another feature or aspect of an embodiment is believed at the time of the filing of this patent application to possibly reside broadly in the deoxyribonucleic nucleic acid molecule, where the substituent and the nucleotide are attached to each other by means of a bi-functional coupling reagent.

Yet another feature or aspect of an embodiment is believed at the time of the filing of this patent application to possibly reside broadly in the deoxyribonucleic nucleic acid molecule, which is substituted at least once with a nuclear localization signal (Seq.ID6).

One feature or aspect of an embodiment is believed at the time of the filing of this patent application to possibly reside broadly in a method to make non-coding deoxyribonucleic nucleic acid molecules that are attached to substituents, consisting of the following reaction steps: a. two oligodeoxyribonucleotides that are partially self complementary, and of which at least one is chemically modified, are attached to the chemically modified substituents directly or by means of a bi-functional coupling reagent under suitable conditions, b. subsequently, the purified products of the coupling reaction are allowed to form partial base pairs and hairpin structures by brief heating and cooling on ice, and c. the resulting self complementary overhangs of the partially double-stranded non-coding deoxyribonucleic nucleic acid molecules are ligated to each other or to oligodeoxyribonucleotides that are attached covalently to other substituents, d. followed by exonuclease treatment to degrade non-covalently closed chains of oligodeoxyribonucleotides that are attached to substituents, prior to e. finally purifying the non-coding deoxyribonucleic acid molecules that are attached to substituents.

Another feature or aspect of an embodiment is believed at the time of the filing of this patent application to possibly reside broadly in the method, where oligodeoxyribonucleotides are employed for the attachment of a substituent that are modified by one or several alcylic carboxylic acid-, amine-, thiole-, aldehyde- or maleimide functional groups.

Yet another feature or aspect of an embodiment is believed at the time of the filing of this patent application to possibly reside broadly in the method, where substituents are employed that are modified by one or several alcylic carboxylic acid-, amine-, thiole-, aldehyde- or maleimide functional groups.

One feature or aspect of an embodiment is believed at the time of the filing of this patent application to possibly reside broadly in a use of the deoxyribonucleic nucleic acid molecules as a vaccine in the therapeutic or prophylactic vaccination in humans and higher animals.

Another feature or aspect of an embodiment is believed at the time of the filing of this patent application to possibly reside broadly in the use of the deoxyribonucleic nucleic acid molecules as an adjuvant for immune stimulation in humans and higher animals.

Yet another feature or aspect of an embodiment is believed at the time of the filing of this patent application to possibly reside broadly in the use of the deoxyribonucleic nucleic acid molecules for the preparation of a vaccine for immune stimulation in humans and higher animals, where apart from said deoxyribonucleic nucleic acid molecules, also dumbbell-shaped, linear covalently closed DNA expression constructs that are attached to substituents are comprised.

Yet another feature or aspect of an embodiment is believed at the time of the filing of this patent application to possibly reside broadly in the use of the deoxyribonucleic nucleic acid molecules for the preparation of a vaccine for immune stimulation in humans and higher animals, where the substituent of the dumbbell-shaped, linear covalently closed DNA expression constructs is selected from the group of peptides, proteins, saccharides, antigenic structures, DNA and/or RNA.

One feature or aspect of an embodiment is believed at the time of the filing of this patent application to possibly reside broadly in a DNA expression vector which is substituted at least once with a nuclear localization signal (Seq.ID6).

Another feature or aspect of an embodiment is believed at the time of the filing of this patent application to possibly reside broadly in the use of the vaccine in the therapeutic or prophylactic vaccination in humans and higher animals.

Yet another feature or aspect of an embodiment is believed at the time of the filing of this patent application to possibly reside broadly in the use of the vaccine as an adjuvant, where the immune stimulation in humans and higher animals can be effected in-vitro or in-vivo.

At least one embodiment of the invention relates to a substituted, non-coding nucleic acid molecule for modulating the activity of the human or animal immune system, a method for the production thereof, and a vaccine containing said substituted, non-coding nucleic acid molecule. The part concerning the invention consists of covalently coupling substituents to said carrier module and the novel properties resulting therefrom, the substituents being coupled to any nucleotides of the stem or the loops, i.e. hairpin-shaped loops. The inventive nucleic acid molecules can also be a component of a vaccine that is used for modulating the immune response in humans or higher animals. Also disclosed is a vaccine comprising a combination of inventive nucleic acid molecules and substituent-coupled, dumbbell-shaped, linear covalently closed expression constructs. Said combination vaccine can also be used as an adjuvant in the therapeutic or prophylactic vaccination of humans or higher animals or for in vitro or in vivo immune stimulation in humans or higher animals.

The components disclosed in the various publications, disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications and publications recited herein, and in the Declaration attached hereto, are hereby incorporated by reference as if set forth in their entirety herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

All of the patents, patent applications or patent publications, which were cited in the international search report mailed Nov. 12, 2004, and/or cited elsewhere are hereby incorporated by reference as if set forth in their entirety herein as follows: WO 02/060476 A; WO 01/07055 A; WO 03/031469 A; WO 03/031470 A; SCHIRMBECK R ET AL: "Priming of immune responses to hepatitis B surface antigen with minimal DNA expression constructs modified with a nuclear localization signal peptide" JOURNAL OF MOLECULAR MEDICINE, vol. 79, no. 5-6, June 2001 (2001-06), pages 343-350; WITTIG B ET AL: "THERAPEUTIC VACCINATION AGAINST METASTATIC CARCINOMA BY EXPRESSION-MODULATED AND IMMUNOMODIFIED AUTOLOGOUS TUMOR CELLS: A FIRST CLINICAL PHASE I/II TRIAL" HUMAN GENE THERAPY, vol. 12, no. 3, Feb. 10, 2001 (2001-02-10), pages 267-278; SCHMIDT MANUEL ET AL: "Immune-modulatory function of CpG sequence motifs in covalently-closed, double-stem-loop DNA constructs (dSLIM)," BLOOD, vol. 102, no. 11, Nov. 16, 2003 (2003-11-16), pages 769a-770a.

The corresponding international patent publication applications, namely, International Application No. PCT/DE2004/001096, filed on May 19, 2004, having WIPO Publication No. WO2005/080567 and inventors Brzezicha et al., and International Application No. PCT/DE2004/000361, filed on Feb. 20, 2004, are hereby incorporated by reference as if set forth in their entirety herein for the purpose of correcting and explaining any possible misinterpretations of the English translation thereof. In addition, the published equivalents of the above corresponding international patent publication applications, and other equivalents or corresponding applications, if any, and the references and documents cited in any of the documents cited herein, such as the patents, patent applications and publications, are hereby incorporated by reference as if set forth in their entirety herein.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

---

What is claimed is:

1. A non-coding nucleic acid molecule comprising;
a partially single-stranded, dumbbell-shaped covalently closed chain of deoxyribonucleotide residues and contains one or more sequences of the base sequence $N^1N^2CGN^3N^4$ in its single or double stranded region, where CG contains an unmethylated Cytosine, where $N^1N^2$ is an element chosen from the group comprising GT, GG, GA, AT or AA, $N^3N^4$ is an element chosen from the group comprising CT or TT, and C is deoxycytosine, G is deoxyguanosine, A is deoxyadenosine and T is deoxythymidine, wherein one or more substituents are covalently attached to said non-coding nucleic acid molecule.

2. The deoxyribonucleic acid molecule of claim 1, wherein the one or more substituent is selected from a group of compounds consisting of peptides, proteins, saccharides, antigenic structures, DNA and RNA.

3. The deoxyribonucleic nucleic acid molecule of claim 2, wherein when more than one substituent is present, they may be selected from the same or different compounds.

4. The deoxyribonucleic nucleic acid molecule according to claim 3, wherein when more than one substituent is present from the same compound they may be identical or different from each other.

5. The deoxyribonucleic nucleic acid molecule according to claim 4, wherein the substituents and the nucleotides are chemically modified and covalently attached to each other.

6. The deoxyribonucleic nucleic acid molecule according to claim 5, wherein the substituents and the nucleotides are attached to each other by means of a bi-functional coupling reagent.

7. The deoxyribonucleic nucleic acid molecule according to claim 6, which contains at least one substituent with a nuclear localization signal of SEQ ID NO 6.

8. A vaccine composition for immune stimulation in humans and higher animals, comprising: a non-coding nucleic acid molecule comprising a partially single-stranded, dumbbell-shaped covalently closed chain of deoxyribonucleotide residues and contains one or more sequences of the base sequence $N^1N^2CGN^3N^4$ in its single or double stranded region, where CG contains an unmethylated Cytosine, where $N^1N^2$ is an element chosen from the group comprising GT, GG, GA, AT or AA, $N^3N^4$ is an element chosen from the group comprising CT or TT, and C is deoxycytosine, G is deoxyguanosine, A is deoxyadenosine and T is deoxythymidine, wherein one or more substituents are covalently attached to said non-coding nucleic acid molecule; and a suitable carrier.

9. The deoxyribonucleic nucleic acid molecule according to claim 1, wherein: in the case of covalent attachment of more than one substituent, these are selected from the same or different groups; and several substituents originating from the group of peptides, proteins, saccharides, antigenic structures, DNA and/or RNA are identical or different from each other.

10. The deoxyribonucleic nucleic acid molecule according to claim 1, wherein at least one of: chemically modified substituents and/or chemically modified nucleotides are covalently attached to each other; and the deoxyribonucleic nucleic acid molecule is substituted at least once with a nuclear localization signal of SEQ ID NO 6.

11. The deoxyribonucleic nucleic acid molecule according to claim 1, wherein: the substituent and the nucleotide are attached to each other by means of a bi-functional coupling reagent; and the deoxyribonucleic nucleic acid molecule is substituted at least once with a nuclear localization signal of SEQ ID NO 6.

* * * * *